(12) United States Patent
Cheung

(10) Patent No.: US 7,736,845 B2
(45) Date of Patent: *Jun. 15, 2010

(54) METHOD TO TREAT COLLAGENOUS CONNECTIVE TISSUE FOR IMPLANT REMODELED BY HOST CELLS INTO LIVING TISSUE

(76) Inventor: David T. Cheung, 10 W. Palm Ave., Arcadia, CA (US) 91007

( * ) Notice: Subject to any disclaimer, the term of this patent is extended or adjusted under 35 U.S.C. 154(b) by 881 days.

This patent is subject to a terminal disclaimer.

(21) Appl. No.: 11/345,768

(22) Filed: Jan. 19, 2006

(65) Prior Publication Data

US 2006/0127876 A1    Jun. 15, 2006
US 2010/0041010 A9    Feb. 18, 2010

Related U.S. Application Data

(62) Division of application No. 10/253,017, filed on Sep. 23, 2002, now Pat. No. 7,008,763.

(51) Int. Cl.
*A61F 2/04*    (2006.01)
*A61F 2/08*    (2006.01)

(52) U.S. Cl. .................. 435/1.1; 600/35; 623/13.17
(58) Field of Classification Search ............... None
See application file for complete search history.

(56) References Cited

U.S. PATENT DOCUMENTS 6,277,555 B1 * 8/2001 Duran et al. ............... 435/1.3
7,008,763 B2 * 3/2006 Cheung ..................... 435/1.1
2004/0057936 A1 * 3/2004 Cheung .................... 424/93.7

* cited by examiner

*Primary Examiner*—Cecilia Tsang
*Assistant Examiner*—Christina Bradley
(74) *Attorney, Agent, or Firm*—Frederick Gotha

(57) ABSTRACT

The invention relates to a method of treatment of collagenous connective tissue removed from a donor for implant into a recipient which is re-habited or re-colonized by host cells without an immune rejection and inflammatory reaction. After removal from the donor the tissue is trimmed and thereafter soaked in a cold stabilizing solution having a temperature range of 4 to 10 degrees centigrade. The tissue is then soaked at a predetermined temperature in a polyglycol, salt, hydrogen peroxide, and phosphate buffer first solution of predetermined quantities and concentrations and of sufficient ionic strength to permit ground substances to dissociate such that the collagen fibers remain stable. The tissue is then soaked in an alcohol and water solution at a predetermined temperature for a sufficient period of time to remove the residue of the first solution. Following the removal of the residue, the tissue is soaked at a predetermined temperature in a third solution of an anti-inflammatory agent, an anti-thrombic agent, alcohol, and water or sequentially in an anti-inflammatory agent, alcohol, and water solution, and then in an anti-thrombic agent, alcohol and water solution and thereafter stored.

28 Claims, 1 Drawing Sheet

METHOD TO TREAT COLLAGENOUS CONNECTIVE TISSUE FOR IMPLANT REMODELED BY HOST CELLS INTO LIVING TISSUE

This Application is a Divisional Application of Prior application Ser. No. 10/253,017, filed Sep. 23, 2002 now U.S. Pat. No. 7,008,763.

FIELD OF THE INVENTION

The present invention relates to a process for treating collagenous connective tissue from an animal donor for implant in an animal or human recipient.

BACKGROUND OF THE INVENTION

The present invention relates to a process for treating collagenous connective tissue or structural support tissue removed from an animal donor for implant into a recipient without an immune and inflammatory rejection. Collagenous connective tissue or structural support tissue may be heart valve tissue, blood vessel, pericardium, omentum, fascia, tendon, ligament, intestine, cartilage, bone, membrane, or other such tissue.

Implants from animal donors into a human recipient to correct defective body components are known in the prior art. For instance, hemostatic collagen implants and collagen injections have been used for hemostasis and tissue augmentation; homograft and xenograft tissue heart valves have been widely implanted with variable results. The implant materials for these procedures were derived from animal origins that contained collagen, elastin, pericardium, and cells along with the proteins and other substances within the extracellular matrices. In the prior art the treatment of the implant depended upon its intended use. Implant materials generally were either intended for temporary implant or for permanent incorporation by the recipient. As an example of a temporary implant, hemostatic collagen may be used for emergencies to arrest blood loss; once hemostasis occurs, there is no further utility for the collagen. The concern where the implant is temporary is that major complications such as infection, pyrogenic shock or a major foreign body reaction by the recipient might occur. Another example of a temporary implant is the absorbent suture which is intended for temporary use so as to permit a wound to heal as the tissue regains its strength. Where the temporary implant material is derived from an animal, the implant material need not be homogeneous; it can be denatured and slightly toxic to the recipient.

Implant materials intended for permanent or long lasting implantation may provide structural support for a body part or may be an active functional organ such as a kidney, liver, or heart. For active functional organs, an immune compatible organ is most desirable. Preferably, it is harvested from a donor whose tissue closely matches that of the recipient.

In the case of permanent structural support, implants derived from biological sources are treated in the prior art before implantation utilizing one of three basic strategies.

The first basic strategy involves chemical modification, i.e., chemical modification of functional groups of tissue components, crosslinking, surface modification, etc. It can also increase the mechanical strength as well as the durability of the tissue by adding crosslinking to tissue fibers. Chemical modification can reduce the antigenicity and alter other properties of the tissue when it is transplanted into a different species. One of the most successful modifications of connective tissue for use as a bioprothesis is the glutaraldehyde fixation or crosslinking of porcine heart valves and bovine pericardium. However, there are limitations on this technology. Glutaraldehyde treated tissue has been shown to be toxic and host cells will not infiltrate tissue subjected to this treatment. The physical properties of glutaraldehyde treated tissue are very different from the physical properties of native untreated tissues. In the case of glutaraldehyde treated tissue for a heart valve prosthesis, calcification is known to be a major cause of valve failure. Numerous methods have been developed to modify the physical properties of glutaraldehyde treated tissue to overcome these limitations. These methods include but are not limited to the following:

a) treatment with detergent or surfactant after glutaraldehyde crosslinking;

b) covalently binding diphosphonates to the glutaraldehyde treated tissue;

c) covalently binding amino-substituted aliphatic functional acid to the glutaraldehyde treated tissue;

d) covalently binding sulfated polysaccharides, especially chondroitin sulfate after glutaraldehyde crosslinking;

e) treatment with ferric or stannic salts either before of after glutaraldehyde crosslinking;

f) incorporation of polymers, especially elastomeric polymers, into the glutaraldehyde treated tissue; or g) immersing glutaraldehyde treated tissues in solutions of a water-soluble phosphate ester or a quaternary ammonium salt or a sulfated higher aliphatic alcohol.

None of these methods, however, has been entirely successful.

The second basic strategy for long-term implantation involves making a piece of tissue with no vital cells. Some examples of this are the following:

a) Decellularization (killing cells by hypotonic shock then followed with nucleases). Goldstein, U.S. Pat. Nos. 5,613, 982; 5,632,778; 5,899,936 and 5,843,182;

b) Controlled autolysis Jaffe, U.S. Pat. Nos. 5,843,180; 5,843, 181 and 5,720,777;

c) Killing of cells by radiation, as shown in Schinstein, U.S. Pat. Nos. 5,795,790; 8,843,431; 5,843, 717 and 5,935,849; and Badylak, U.S. Pat. No. 6,126,686); peracetic acid (Badylak U.S. Pat. No. 6,126,686);

d) Acid treatment (Abraham, U.S. Pat. No. 5,993,833); and e) Other processes in the prior art construct composites of purified collagenous material with a synthetic scaffold (Bell, U.S. Pat. No. 6,051,750). The objective of all of these methods is to create a matrix that the host can accept such that cells in the recipient's body can migrate into the matrix and eventually remodel the material into a living tissue.

The third strategy involves the preservation or incorporation of living cells in the transplanted material. Tissues removed from the donors have a finite time limit before cells in the tissues die due to autolysis as a result of lack of oxygen. Conditions such as lowering the temperature and placing the tissues in solutions containing ischemic protection agents can keep cells vital for an extended time. Cryopreservation has been used to preserve the vitality of cells in tissues to an even longer time. However, the number of cells that survive in a host is substantially affected by the time lapse between harvesting and cryopreservation, and by the length of time the tissue has been preserved, by the thawing process and the implant procedures. The surviving cells will thereafter face a very hostile environment in the host unless there is a close genetic match or there is initiated an immune suppressive therapy.

The treatment of scaffold material to form living tissue outside the host has become a popular research topic. In an incubation environment, in order to have enough cells to infiltrate and grow in the scaffold material, the cells must be able to or stimulated to divide and grow rapidly.

To transition from a growing to a stable phase, such rapidly dividing and growing cells must be controlled. Once the cells are controlled, whether they will remain controlled after implant in the host is a major concern under this third strategy. The basic limitation that pervades this third strategy of the prior art is the lack of a sterilization method that can preserve living mammalian cells.

While the third strategy either keeps the cells from the donor alive or utilizes facilities outside of the recipient's body to culture or incubate living cells into the implants, by contrast the second strategy utilizes the recipient's cells as the donor source for cells and the recipient's body environment as an incubator. The current invention provides a process where implant materials will interact with the recipient's body without an immune and inflammatory rejection and the body cells will migrate to the implant to remodel the implant into living tissue.

Immune rejection is a major problem in transplantology. The major cause of immune rejection is the difference between the cell surface molecules of the donor and the recipient. If the implant contains donor living cells, this problem is prolonged and amplified as long as the donor cells are living and proliferating. If the implanted tissue does not contain living cells, the dead cells still present a problem. For this reason, methods have been developed to extract the remnants of dead cells from tissue through the use of detergents, solvents, etc. Such methods require extraction to be very aggressive to ensure that all the unwanted materials are extracted. Under such harsh conditions, tissue matrix components which are critical to the integrity of the tissue are also destroyed. The destruction of the tissue matrix components can be subtle and difficult to detect and often not easily observed using light microscopy or electron microscopy.

It has been suggested in the prior art that polyethylene glycol (PEG) may reduce immune response of recipients to allogeneic transplants ("Heart Preservation Solution Containing Polyethylene Glycol: An Immunosuppressive Effect" by Collins, et al. in Lancet, 338:390 (1991)). In one study a 30% reduction has been observed in the incidence of acute rejection in a group of heart transplant recipients in which the donor organ had been stored at 4° C. in a solution containing 5% PEG. In a subsequent study, PEG produced a modest but statistically significant increase in rat liver allograft survival time from 9.6 to 11.9 days (see "The Immunosuppressive Effect of Polyethyene Glycol in a Flush Solution for Rat Liver Transplantation" by Tokunaga, et al. in Transplantation, 54:756-8 (1992)). In these studies, the transplant organ was merely soaked in the PEG solution without subsequent cryopreservation. In U.S. Pat. No. 4,938,961, Collins, et al., discloses an organ preservation solution containing polyethylene glycol, along with a variety of further ingredients including: 30-40 mM NaOH, 100 mM lactobionic acid, 25 mM $KH_2PO_4$, 10 mM KOH, 30 mM raffinose, and 3 mM glutathione. This solution is used for the transport of an organ from a donor to a recipient. U.S. Pat. No. 6,280,925 to Bruckbank discloses a tissue pretreatment solution containing PEG and glutathione for use prior to cryopreservation. In the current invention, by incubating PEG with tissues under a high ionic strength condition, the collagen molecules remain insoluble but the interaction between proteoglycans and collagens is weakened. In this manner, proteoglycans on the surface of collagen fibers are replaced by PEG while preventing the collagen fibers from collapsing and aggregating.

While it is important to remove and mask substances antigenic to the recipients, it is also important to consider other factors relevant to the behavior and survival of the implanted materials. Acute and chronic inflammation are major defense mechanisms our bodies use against foreign invading materials as well as removing damaged materials resulting from injury or cell death. The mechanisms are initiated by inflammatory cells arriving at the site of foreign material. They digest the foreign material by oxidation. The digested material or the digestion process further recruits more inflammatory cells. As a result, the cycle continues until all the foreign or damaged "wounded self" materials are removed. Very often, an acute inflammatory reaction can cause damaged tissues to be even more vulnerable to further recruitment of inflammatory reaction thereby resulting in chronic inflammation. An example is chronic arthritis; inflammatory cells continue to attack an already inflamed joint matrice from previous injury or disease. The inflamed tissues recruit a further inflammatory reaction which damages the joint matrice even further and results in a vicious cycle that leads to a permanent disabling of the joint. In most cases, inflammatory reactions subside as the injured tissue or foreign bodies are cleared from the recipient. In the field of implantable biomedical implants, long term success of an implantable biomaterial depends on the host prevention of the inflammatory reaction against the implant.

In the present invention, the foreign implant becomes acceptable to the host or recipient by a process that renders the implant less oxidizable and thus less inflammatory. This is achieved in part by using hydrogen peroxide to oxidize the foreign implant.

Thus, the present invention provides a process for treating collagenous connective tissue such that the tissue is implantable without an immune and inflammatory rejection. The process permits the collagen matrix to remain intact and permits the residual antigenic components to be masked by polyethylene glycol; the process permits collagen fibers to remain structurally viable and the tissue to be oxidized to reduce recruitment of inflammatory cells; the process permits the tissue to incorporate water insoluble anti-inflammatory agents that inhibit the arrival of inflammatory cells at the implant site, and permits the tissue fibers to absorb an antithrombosis agent on their surface.

SUMMARY OF THE INVENTION

There is, therefore, provided according to the present invention, a method for processing collagenous connective tissue from an animal donor source such that the collagen fibers may be implanted in a recipient without an immune and inflammatory rejection.

The present invention is directed to a process for treating collagenous connective tissue that permits the collagen fibers to remain structurally intact and permits the tissue to be implanted in the recipient without an immune and inflammatory rejection. After removal from the donor, the collagenous connective tissue is trimmed in saline and thereafter the collagen fibers are stabilized in a cold stabilizing solution having a temperature range of 4 to 10 degrees centigrade. The cold stabilizing solution may be a saline solution where the collagen fibers are soaked preferably for a period less than 48-hours, or an alcohol/water solution where the soaking time preferably does not exceed 30 days. After the tissue is stabilized, it is submerged and soaked in a solution comprised of polyglycol, a salt, a phosphate buffer, and an oxidizing agent. The concentration of the polyglycol is in the range of 1% to 15% and its molecular weight may be in the range of 2,000 Daltons to 20,000 Daltons; the salt concentration may be in the range of 2.5M-4.5M (moles per liter of solution). The phosphate buffer is selected from the group consisting of sodium phosphate and potassium phosphate. It is preferable that the buffer have a concentration of 0.05M with a pH of 7.4. However, the pH may have a range between 6.5 and 7.8 and the concentration may range from 0.02 to 0.1M; and the oxidizing agent preferably is hydrogen peroxide having a concentration in the range of 0.1% to 2%. Ozone may also be used as an oxidizing agent in an another method in a concentration range of 1-500 ppm, preferably in the range of 20-40 ppm.

Following soaking in the first or masking solution, the tissue is washed in a second solution comprised of alcohol and water where the alcohol may be selected from the group consisting of ethanol, iso-propanol, n-propanol, and combinations of different alcohols.

After washing the residue remaining on the tissue from soaking in the polyglycol, salt, phosphate buffer and oxidizing agent solution, the tissue is further soaked in a third solution containing alcohol, water and an anti-inflammatory agent selected from the group consisting of indomethacin, ibuprofin, aspirin, choline salicylate, difunisal, magnesium salicylate, magnesium choline salicylate, salsalate, flurbiprofen, fenoprofen, ketoprofen, naprosen, naproxen sodium, oxaprozin, diclofenac sodium, diclofenac misoprostol, etodolac, indocin, ketorolac, natumetone, sulindac, tolmetin, sulfinpyrazone, dipyridamole, ticlopidine, valdecoxib, rofecoxib, piroxicam, meloxicam, meclofenamate sodium, mefenamic, cyclophosphamide, cyclosporine micromulsion, chlorambucil, anagrelide, clopidogrel, and cilostazol, where the concentration of the anti-inflammatory agent is in the range of 10 to 200 mg/liter. Following soaking in the third solution, the tissue is further soaked in a solution of alcohol, water and an anti-thrombic agent which may be selected from the group consisting of heparin, ardeparin, enoxaparin, tinzaparin, danapariod, lepiruden and hirudin. The concentration of the anti-thrombic agent may be in the range of 100 to 1,000 IU/ml.

In an alternative method, after washing, the tissue may be soaked in a solution of alcohol, water, an anti-inflammation agent, and an anti-thrombic agent having a concentration in the range of 100 to 1,000 IU per ml. The anti-inflammatory agent and anti-thrombic agent in the alternative method are selected from the same groups identified above.

In another alternative method, for non-cardiovascular applications such as orthopedics, neurological, and urological applications, after washing, the tissue is soaked in an anti-inflammatory solution containing alcohol, water and an anti-inflammatory agent selected from the group consisting of indomethacin, ibuprofin, aspirin, choline salicylate, difunisal, magnesium salicylate, magnesium choline salicylate, salsalate, flurbiprofen, fenoprofen, ketoprofen, naprosen, naproxen sodium, oxaprozin, diclofenac sodium, diclofenac misoprostol, etodolac, indocin, ketorolac, natumetone, sulindac, tolmetin, sulfinpyrazone, dipyridamole, ticlopidine, valdecoxib, rofecoxib, piroxicam, meloxicam, meclofenamate sodium, mefenamic, cyclophosphamide, cyclosporine micromulsion, chlorambucil, anagrelide, clopidogrel, and cilostazol.

DETAILED DESCRIPTION

Figure 1:
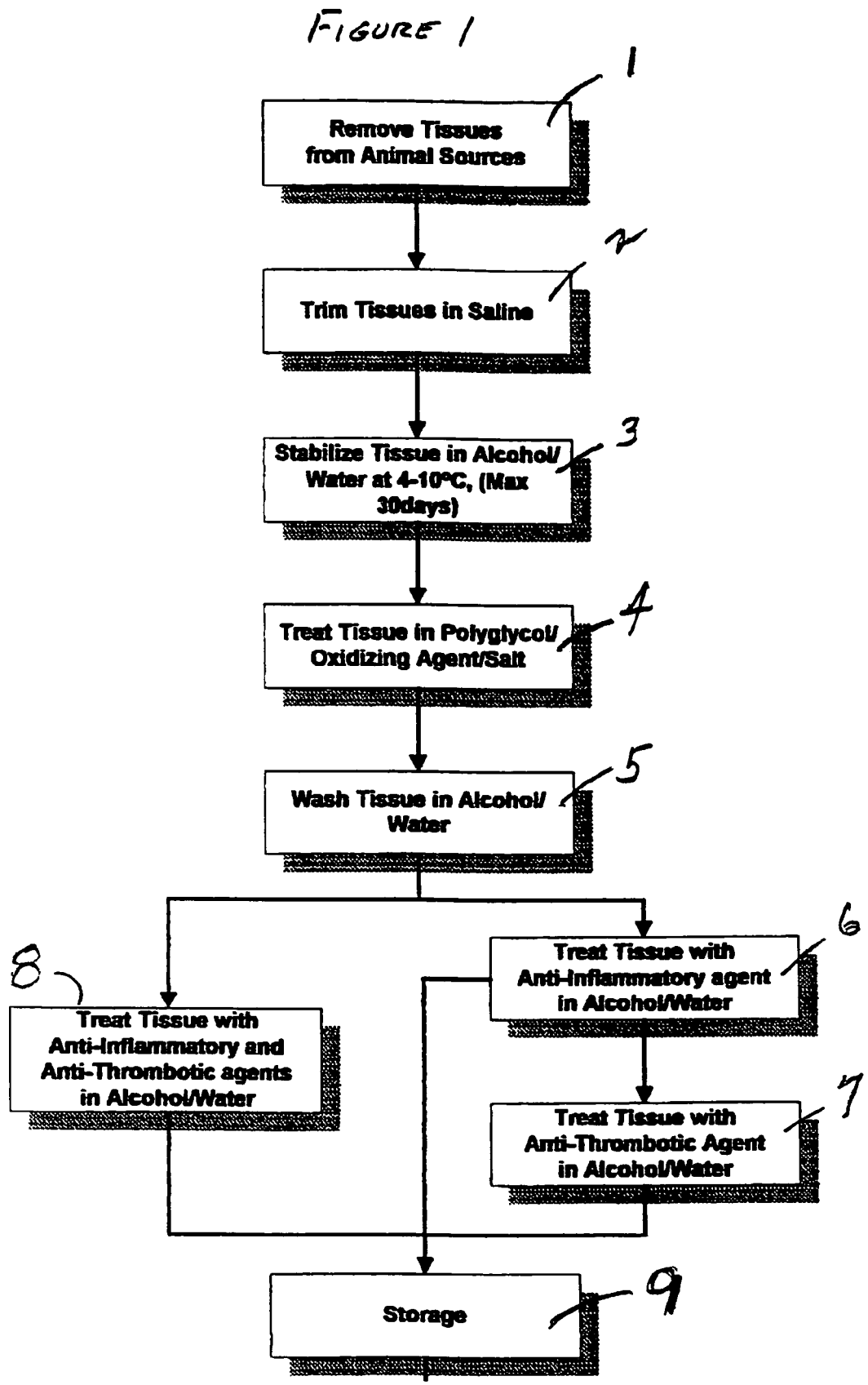
FIG. 1 is a schematic illustrating the steps comprising the method for processing collagenous connective tissue taken from an animal donor for implant into a recipient without an immune rejection and an inflammatory rejection.

The major defense mechanism against the implant of foreign tissue or against injured and dead host cells is commonly known as acute and chronic inflammation. Inflammation occurs when the recipient's defense mechanism recognizes the foreign tissue or injured or dead host cells and recruits inflammatory cells such as macrophages and polymorphonucleocytes. Upon the arrival of inflammatory cells at the invasive site, the host body secretes inflammatory granules containing enzymes that digest the foreign materials by an oxidation process. This digestion process recruits even more inflammatory cells and as a result the cycle continues until all of the foreign materials or damaged cells are removed. In most cases, the inflammatory reaction subsides as the injured tissue or invading foreign body is cleared from the recipient; this usually means that the inflammatory site is depleted of the foreign material that had the potential of being further oxidized.

In the field of implantable biomedical implants, long-term success of an implantable biomaterial depends on the strength of the host inflammatory reaction. The present invention is directed toward a process which renders the implant less oxidizable and thus essentially eliminating an inflammatory condition.

A key oxidizing component of the inflammatory cell and the inflammatory granule is the free radical oxygen molecule in the form of a peroxide. The current invention utilizes hydrogen peroxide as an oxidant which is the same oxidant naturally generated in a host body during inflammatory reactions. Hydrogen peroxide is capable of oxidizing a number of biological molecules within oxidizable functional groups such as aldehydes, amines, lipids and fats. Because the initial oxidation reaction can cause the denaturation of tissue fibers, resulting in damaged tissue, it is desirable and necessary to protect the tissue fiber while the oxidation reaction is carried out. It has been found that collagen molecules and fibers in animal tissue are very stable in salt concentrations above 3 Normal at neutral pH. Under such conditions, collagen is not soluble but if previously solubilized, will precipitate. In the present invention, this condition is utilized to stabilize the tissue while the oxidation reaction is carried out.

To render an implant less inflammatory, the present invention utilizes an anti-inflammatory agent which is incorporated into the implant. However, there are a number of anti-inflammatory agents widely used in medicine that produce unwanted side effects. For instance, steroidal anti-inflammatory drugs such as Glucocorticoids derived from structures of steroids possess biological characteristics that will result in such side effects. Likewise, some non-steroidal agents are undesirable because they vary in their action and effectiveness. Soluble drugs are also undesirable for incorporation in an implant because they are cleared from the implant too quickly. In the present invention anti-inflammatory drugs are chosen which are not easily soluble or quickly cleared from the implant. It has been found that when indomethacin or other anti-inflammatory agents are dissolved in 50% ethanol, they will penetrate well-preserved biological matrices. Also, since indomethacin has a very low solubility in water, the infiltrate indomethacin will be cleared from the implanted material very slowly.

Connective tissue is composed mainly of collagen, elastin fibers, collagenous proteins, proteoglycans, lipids and nucleic acids, small soluble organic molecules, minerals, salts and water. When extracting non-collagen materials from implant tissue, the small substances can easily be washed away unless within living cell. In such case, killing the cell will release the substances to the extracellular space and thus make them easily removable. However, the larger substances such as proteins, proteoglycans, and nucleic acids are more difficult to remove. A classical way to purify collagen is to subject the collagen to a high concentration of salt. This causes the collagen to precipitate while the proteoglycans and nucleic acids are soluble. The high salt concentration also breaks the interaction of proteoglycans and nucleic acids and their propensity to cling to collagen. Thus, soaking tissue in high salt concentrations removes certain non-collagenous material while keeping the tissue intact. To facilitate removal of non-collagenous material inside cells, the tissue may first be treated in ethanol which destroys and extracts the lipid membrane of cells.

The integrity of the collagen molecules and fibers in tissue must be protected while the non-collagenous material is being extracted and the remaining material is oxidized. Polyethylene glycol (PEG) at a concentration of 4% has been found to precipitate collagen and can be used in tissue cultures to keep newly sensitized collagen insoluble. In case of cell cultures, because the cells are attached to the bottom of a plastic dish or a support surface, a large volume of medium is poured on top to feed the cells which promotes an environment similar to conditions inside a recipient body. Unlike cells surrounded by a tissue matrix environment in a living organism, most of the collagen made by cells is released into the medium on top of the cells. In order to analyze the collagen made by the cells and avoid dealing with large volumes of medium, PEG is added and it has been found that this results in all of the collagen remaining at the bottom of the dish. Thus, as the collagen is shipped outside of the cells, it is kept insoluble by the PEG and cannot float away. Since PEG binds to collagen and other proteins tightly, it acts naturally as a masking agent of non-extracted antigenic sites in the tissue.

FIG. 1, schematically presents the process of this invention and its embodiments. Schematics 1 and 2 identify the steps of removal and trimming of tissue that has been harvested from an animal donor. After harvesting, the tissue is kept from being degraded by placing the tissue in a physiological saline solution at low temperature, preferably 4-10 degrees centigrade for a period not to exceed 48 hours. Blood and other soluble substances are rinsed away using large volumes of cold saline and the excess tissue is trimmed away. Collagen matrix in physiological saline with the proper pH and low temperature is stable and proteolytic (enzymatic degradation of collagen matrix) activities resulting from cell death can also be minimized under such conditions.

Referring now to schematic 3 of FIG. 1, it is therein indicated that the tissue may be stabilized in an alcohol/water solution for a period not to exceed 30 days at a temperature in the range from 4 to 10 degrees centigrade. Since collagen is not soluble in 50% ethanol, the collagen molecules cannot unwind from the collagen fibers contained in the tissue. Intact collagen fibers are stable against most degradative activities which are also fixed and inactivated in 50% ethanol. The tissue may be stabilized in a cold stabilizing solution when the solution is a saline solution; however the soaking period in a saline solution should preferably not exceed 48 hours but may be extended to 72 hours. Where the cold stabilizing solution is an alcohol and water solution, the soaking period should be for a period less than 30 days.

After the tissue is treated in the stabilizing solution, the tissue is then transferred into a first solution, as indicated in schematic 4, that is comprised preferably of polyethylene glycol (PEG)5% (molecular weight 8,000), 0.5-0.6% hydrogen peroxide, 4 M salt, and sodium phosphate or potassium phosphate at 0.05M, pH 7.4 and incubated or soaked at a temperature of preferably 4 degrees C. for a period of 96 hours. In the preferred method, the ratio of solution to tissue is greater than 50 cc/2 gm of tissue to ensure that the tissue is submerged in the solution and that the treatment is complete. This could be accomplished at ratio in the range of 25 cc up to 2 liters.

At concentrations of PEG greater than 15%, host cells will fuse and thus concentrations above this level are to be avoided. High concentrations of PEG have been used to fuse mouse myeloma cells and mouse spleen cells in the production of monoclonal antibodies. Likewise, higher concentrations of hydrogen peroxide in excess of 2% are to be avoided to prevent excessive oxidation. The preferred concentration of hydrogen peroxide is 0.5 to 0.6%. Hydrogen peroxide in the range of 0.1 to 2% may be used for the treatment of tissue in the process of this invention. In another embodiment the oxidizing agent may be ozone having a preferable concentration of 20-40 ppm; however, the range of concentration may be from 1-500 ppm.

The polyglycol identified in schematic step 4 may be polyethylene glycol, polypropylene glycol or derivatives of these polymers. The preferred molecular weight of the polyglycol is 8,000 Daltons; however, the molecular weight of the polyglycol may be in the range of 2,000 to 20,000 Daltons. As previously stated, the preferred concentration of polyglycol is 5%; the concentration of polyglycol in the solution may vary however between 1% and 15%. The salt referred to in schematic 4 is preferably sodium chloride with a concentration between 2.5 to 4.5 M. The salt can be selected from the group consisting of sodium chloride, potassium chloride, sodium bromide, potassium bromide, sodium sulfate, potassium sulfate, ammonium chloride and ammonium sulfate. The phosphate buffer is selected from the group consisting of sodium phosphate and potassium phosphate. It is preferable that the buffer have a concentration of 0.05M with a pH of 7.4. However, the pH may have a range between 6.5 and 7.8 and the concentration may range from 0.02 to 0.1M. When soaking the tissue in the first solution containing the predetermined quantities of polyglycol, oxidizing agent, salt and phosphate buffer as above recited, the solution will be of sufficient ionic strength to cause ground substances to dissociate from the tissue while the collagen fibers remain intact. The tissue preferably should be soaked in the polyglycol, oxidizing agent, salt and phosphate buffer solution for a period of 96 hours; however, it has been found that the tissue may alternatively be soaked for periods in the range of 12 hours to 14 days.

After treating the tissue described in schematic 4 above, the tissue is then washed in an alcohol/water solution as indicated in schematic 5. In the washing step set forth in schematic 5, the salt in the tissue is washed away by 50% ethanol preferably until a negligible amount of salt is left in the tissue. The concentration of alcohol may be between 25% to 70% and the alcohol may be ethanol, iso-propanol, n-propanol or combination of these different alcohols. It is preferred that the temperature of the alcohol be at 4 degrees centigrade however the washing range may be from 4 to 25 degrees centigrade and the time for washing may be as long as 30 days. It is preferred that the washing occur overnight or approximately for 16 hours.

After the washing step referred to in schematic 5, the tissue is further soaked in a 50% ethanol solution containing 20 mg/liter of indomethacin and 250 IU/ml of heparin. In non-cardiovascular applications (for example, tendons and ligaments, conduits for nerve guides, tissue membranes such as tissue patches, urological conduits, etc.) heparin is not needed and can be omitted. The amount of indomethacin or anti-inflammatory agent should be in the range used for humans on a dose/kg body weight basis. High dosages of the anti-inflammatory agent are to be avoided because the tissue can be damaged and become toxic to host cells.

Referring now to schematics 6, 7, and 8, it can be seen that after the step of washing the tissue in alcohol/water as stated in schematic 5, the tissue may be treated before storage in any of 3 separate ways: (1) tissue may be sequentially treated as shown in schematic 6 followed by schematic 7; (2) the tissue may be treated as indicated in schematic 6 and then sent to storage; (3) or the tissue may be treated as described in schematic 8 and then sent to storage. The preferred treatment is the treatment described in schematic 8 where the tissue is treated in a solution containing both anti-inflammatory and anti-thrombotic agents in alcohol/water. Although endomethycin and heparin are the preferred ant-inflammatory and anti-thrombotic agents, there are numerous other such agents that might be used. For instance, the anti-inflammatory agent may be an analgesic or anti-pyretic selected from the group consisting of indomethacin, ibuprofin, aspirin, choline salicylate, difunisal, magnesium salicylate, magnesium choline salicylate, salsalate, flurbiprofen, fenoprofen, ketoprofen, naprosen, naproxen sodium, oxaprozin, diclofenac sodium, diclofenac misoprostol, etodolac, indocin, ketorolac, natumetone, sulindac, tolmetin, sulfinpyrazone, dipyridamole, ticlopidine, valdecoxib, rofecoxib, piroxicam, meloxicam, meclofenamate sodium, mefenamic, cyclophosphamide, cyclosporine micromulsion, chlorambucil, anagrelide, clopidogrel, and cilostazol; the anti-thrombic agent may be an anti-coagulant selected from the group consisting of heparin, ardeparin, and enoxaparin, tinzaparin, danapariod, elpiruden and hirudin.

The concentration of the anti-inflammatory agent in schematics 6, 7 or 8, is preferred to be 20 mg per liter; however, the concentration may be in the range of 10 mg to 200 mg per liter. The soaking time preferred in schematics 6, 7, and 8 is preferred to be 24 hours to allow the agent to penetrate the tissue uniformly.

After the treatment of tissue as set forth above in the embodiments of the methods of this invention, the tissue may be stored as shown in schematic 9. The methods of storage are well known in the prior art and the storage medium preferably would be 50% ethanol with the range of storage temperature between 0° C. and 6° C. to minimize bioburden effects.

The following are examples of tissue treated in accordance with the process of the present invention:

Example 1

Freshly harvested bovine mesenteric arteries were stored in 50% alcohol for one week and then treated (or soaked) in a solution containing 5% PEG (molecular weight 8,000 D), 0.5% hydrogen peroxide, 4 M NaCl and 0.05 M phosphate buffered at pH 7.0 for 96 hours at 4° C. The arteries were washed in 50% ethanol twice and then further treated (or soaked) in a solution of indomethacin (50 mg/l) and heparin (250 IU/ml) in 50% ethanol overnight. The treated arteries were further soaked in 50% ethanol containing 20% glycerol, 5% PEG (MW=10,000), indomethacin (50 mg/l), and heparin (250 IU/ml). The arteries were then freeze-dried using a FTS Durastop/Duratop lyophilyzer system. The freeze-dried arteries were subjected to hydrogen peroxide sterilization by Star Service (Hayward, Calif.) with a Sterrad-100 hydrogen peroxide gas phase sterilizer using a standard validated sterilization program. The tissues were rinsed in saline for 30 minutes before the following studies were done.

1. Shrinkage Temperature—treated arteries have a shrinkage temperature between 62-65° C., which is comparable to fresh untreated graft tissues.

2. Enzyme Digestion—treated arteries are similar to fresh untreated tissue in its ability to resist pepsin digestion. Pepsin digestion of treated arteries for 24 hours at 4° C. released less than 5% of non-salt precipitable hydroxyproline indicating that the collagen fibers in the tissue material are intact after treatment.

3. Tensile Strength—mechanical stress-strain analysis was carried out on nine treated arteries and three fresh untreated control arteries. The test method was designed and conducted according to ANSI/AAMI VP20-1994 Section 8.3.2. The results demonstrate that tensile strength as well as the longitudinal pull strength of Corograft™-D is similar to untreated control bovine mesenteric arteries. The results of these tests demonstrate that the longitudinal tensile strength of treated arteries is similar to the untreated fresh control bovine mesenteric arteries. The mean and standard deviation for the longitudinal tensile strength for the nine treated strengths of 33.2±6.5 Newtons. The mean and standard deviation for the extension of the nine treated arteries was 42.8±4.0 mm beyond the original 50 mm length compared with the controls which had a value of 48.9±3.9 mm extension beyond the original 50 mm length.

4. Compliance—the compliance of treated arteries and untreated control bovine arterial vessels were studied using an in-house test set-up for measuring the Dynamic Compliance in accordance with ANSI/AAMI VP20-1994 Section 8.10. The set-up consists of the Wieting Cardiac Valve Analyzer which provided a pulse rate at 72 beats per minute and physiologic systolic/diastolic pressure ratios adjustable to 80/40, 120/80, 160/120 and 200/160 mm Hg per the FDA Guidance. The change in diameter was measured by means of the SCIMED Coronary Imaging Catheter. The aortic (or input) pressure was measured by means of a Baxter Uniflo Pressure Transducer with Honeywell Electronics for Medicine Pressure Amplifier, which is converted to a digital data input into a computer data acquisition system. The results show that treated arteries has a dynamic compliance similar to untreated bovine mesenteric arteries. The means and standard deviation for the compliance for the nine treated artery samples at a systolic/diastolic pressure ratio of 80/40 mmHg was 6.58±3.24 (% radial change per mmHg) compared with the fresh control which had a compliance value of 8.82±1.65 for ten cycles at the same systolic/diastolic pressure ratio.

5. Suture Retention Strength—suture retention strength of treated arteries reconstituted in saline and fresh untreated bovine arteries was carried out in-house using a Chatillon Universal Tension/Compression Tester Model LTCM-6, (Ametek Test and Calibration Instruments, Largo, Fla.) and an Omegadyne "S" Beam Load Cell Model LC 101-25. The test method was designed and conducted according to ANSI/AAMI VP20-1994 Section 8.8. Prolene 6-0 suture (Ethicon) was used for 90° cut (normally used for proximal anastomosis) and 7-0 was used for 45° oblique cut (normally used for distal anastomosis to the target coronary artery vessel). The mean suture retention force for nine treated artery samples and three untreated control bovine arterial vessels are listed in Table 1 below:

TABLE 1

| | Suture Retention Force (Kg) | | |
| --- | --- | --- | --- |
| | Toe | Heel | Right side |
| 45° C. cut (oblique) | | | |
| Treated arteries | 0.202 ± 0.037 | 0.119 ± 0.042 | 0.199 ± 0.038 |
| Untreated control | 0.206 ± 0.064 | 0.223 ± 0.085 | 0.190 ± 0.028 |
| 90° C. cut (straight) | | | |
| Treated arteries | 0.247 ± 0.058 | 0.272 ± 0.024 | 0.303 ± 0.060 |
| Untreated control | 0.211 ± 0.051 | 0.253 ± 0.042 | 0.248 ± 0.045 |

6. Suture Hole Elongation—a suture hole elongation study of treated arteries and untreated control bovine mesenteric arteries was carried out using the Chatillon Universal Tension/Compression Tester Model LTCM-6. The study was designed and conducted following the FDA Draft Guidance for the Preparation of Research and Marketing Applications for Vascular Graft Protheses (1993) Section 11.1.4. Five continuous loops were placed 2 mm from the 90° cut end of each samples (9 treated arteries and 3 control samples) using Prolene 6-0 suture. Initial test using a 5-mg weight at the other end of the suture loop did not result in any measurable suture hole elongation. The amount of weight used was determined based on a revision of the FDA recommended equation, $WT=5(FL^*)/n$ where $FL^*=PA$ or $P\pi(d/2)^2$ instead of $FL=Pd$. Therefore weights were gradually added in subsequent tests from 0 to 19 grams. The results are shown in Table 2 below.

TABLE 2

| | Suture Hole Elongation at | |
| --- | --- | --- |
| Test sample | 9 grams | 19 grams |
| Treated arteries | 0.04 ± 0.03 mm | 0.09 ± 0.05 mm |
| Control | 0.11 ± 0.03 mm | 0.17 ± 0.01 mm |

These tests indicate that the suture holes in treated arteries did not elongate as much as those in the control grafts.

7. Burst Strength—the burst strength analysis of treated arteries reconstituted in saline and untreated control bovine mesenteric arteries was carried out. The study was designed and conducted according to ANSI/AAMI VP20-1994 Section 8.3.3. The test set-up consists of a pressure reservoir connected to a compressed air supply providing 0-125 psi of pressure via a pressure regulator. One end of a test sample was connected to the outlet of the reservoir and the other end was connected to a pressure transducer (Omega Model PX302-100G) where the output was routed to a computer data acquisition system. During the test, water pressure in the reservoir increased at a rate of approximately 0.07 psi/second until the test sample burst. The mean and standard deviation of the bursting pressure for the nine treated artery samples was 14.7±2.6 psi for the three untreated control bovine mesenteric arteries was 15.2±1.7 psi (greater than seven times the mean normal blood pressure of 100 mm Hg in human). The difference between the bursting pressure for treated arteries and untreated control fresh arteries is not statistically significant.

8. Kink Radius—the kink radius of treated arteries reconstituted in saline was studied (according to ANSI/AAMI VP20-1994 Section 8.9) using an set-up consisting of a series of brass cylinders with diameters of 4.5, 5.5, 7.0, 8.0, 9.0, 10.0, 11.5, 12.5 and 13.5 mm. A static pressure reservoir was used to maintain a hydrostatic bovine mesenteric artery samples show that the average kink radius of treated arteries (5.6±0.8 mm) is about 1.75 mm larger than the control untreated samples (3.8±0.3 mm)

9. Crush Resistance (Philogenesis Protocol No. 019, Test Report No. TR-008)—Crush resistance test of Corograft™-D reconstituted in saline was carried out (following the FDA Guidance for the Preparation of Research and Marketing Applications for Vascular Graft Prothesis, 1993, Section 11.1.6.). The results shows that Corograft™-D has a slightly greater crush resistance force (38.7±0.17.4 g) than control untreated grafts (26.0±5.7 g) at 2 mm (more than 50%) deflection.

10. Cytotoxicity, MEM elution—treated arteries were evaluated by the MEM elution cell culture cytotoxicity test carried out by Nelson Laboratory, Salt Lake City, Utah in accordance with ANSI/AAMI/ISO 10993-5: 1999, 10993-12: 1996, 10993-1: 1997. The results showed that no rounding of cell or cell lysis (mild reactivity) was observed with the artery extracts (24 hours at 37° C.

11. Skin Sensitization Test (ISO Magnusson Kligman Method, 2 extracts—treated arteries were tested using the Skin Sensitization Test (ISO Magnusson Kligman Method) in guinea pigs. This study was subcontracted to NAMSA, Irvine, Calif. by Nelson Laboratory, Salt Lake City, Utah in accordance with ISO 10993-10. Samples were reconstituted (rehydrated) with saline (1.2 g/200 ml PSB) for 5 minutes. The reconstituted samples were then extracted with saline (1.2 g of tissue/6 ml of saline) at 37° C. for 72 hours. Mixtures of extracts, Freund's Complete Adjuvent and SWFI (1:1:2) were injected intradermally in guinea pigs to induce a potential allergic response. Topical applications of the extracts at the injection sites (after 7 days) were used as a second induction. On day 21 the animals were challenged for measurements of an allergic response at day 22-25. The results showed that no evidence of the treated arteries causing delayed dermal contact sensitization in the guinea pig.

12. Skin irrigation Test (ISO intracutaneous reactivity, 2 extracts)—the ISO intracutaneous reactivity of the treated arteries was tested in rabbit. This study was subcontracted to NAMSA, Irvine, Calif. by Nelson Laboratory, Salt Lake City, Utah, and Biological Test Center, Irvine, Calif. according to ISO 10993-10. Samples were reconstituted (rehydrated) with saline (1.6 g/200 ml PSB) for 5 minutes. Reconstituted samples of extracts (1.6 g of samples extracted with 8 ml of saline or cottonseed oil at 37° C. for 72 hours were injected intracutaneously into the dorsal skin of the rabbits (5 sites with 200 ml injection/site in each rabbit). The extracts of treated arteries had a negligible Primary Irritation Index.

13. Systemic Toxicity—ISO system toxicity (mice, 2 extracts)—potential systemic toxicity of the treated arteries was tested on mice. The study was subcontracted to NAMSA, Irvine, Calif. by Nelson Laboratory, Salt Lake City, Utah in accordance with ISO-10993-11. Samples were reconstituted (rehydrated) with saline (1.6 g/200 ml PBS) for 5 minutes. Reconstituted samples of extracts (1.6 g of samples extracted with 8 ml of saline or cottonseed oil at 37° C. for 72 hours) were injected in mice did not cause a decrease in body weight over a period of 72 hours and no mortality or evidence of systemic toxicity from the extracts was observed.

14. Subchronic Toxicity: Intravenous Toxicity with Histopathology—potential subchronic toxicity for the treated arteries was tested in rats. The study was subcontracted to NAMSA, Irvine, Calif. by Nelson Laboratory, Salt Lake City, Utah (according to ISO 10993-11) using the Intravenous Toxicity with Histopathology test. Samples were reconstituted (rehydrated) with saline 6.9 g/200 ml PBS) for 5 minutes.

Reconstituted samples of extracts at 37° C. for 72 hours (6.9 g of sample was covered with 35 ml of saline for extracts on days 1-7, and 7.9 g of sample was covered with 40 ml of saline for extracts on days 8-14). Test animals received an injection of 10 ml/kg (body weight) via the laterial tail vein once each day for 14 consecutive days. There was no significant evidence of systemic toxicity from the extracts of the test article injected intravenously into rats.

15. Genotoxicity, Ames Test (*Salmonella Typhimurium* Reserve Mutation Assay—The Ames Test was conducted by Nelson Laboratory, Salt Lake City, Utah in accordance with ANSI/AAMI/ISO 10993-3:1993, 10993-12:1996, on extracts from treated arteries. Test graft samples were reconstituted in 200 ml of saline for 5 minutes. The reconstituted samples were then extracted by 20 ml of saline at 37° C. for 72 hours. The extracts tested against the five tester strains did not meet the criteria for a potential mutagen.

16. ASTM Hemolysis Test—the treated arteries were tested by Nelson Laboratory, Salt Lake City, Utah (according to ASTM F756-00, July, 2000) using human blood samples. The results showed a 4.8% corrected hemolytic index indicating the device is "slightly hemolytic".

17. Partial Tromboplastin Time Test (PTT Test)—the PTT test was conducted by Nelson Laboratory, Salt Lake City, Utah in accordance with ANSA/AAMI/ISO 10993-4: 1993. Three samples of treated arteries (0.8 g) were incubated in 4.0 ml of human citrated plasma for PTT test. The result showed that there is no clot formation during the 10-minute test interval for any of the 6 replicate samples. This is expected since treated arteries is incorporated within heparin.

18. Prothrombin Time Test (PT Test)—the PT test was conducted by Nelson Laboratory, Salt Lake City, Utah according to ANSI/AAMI/ISO 10993-4:1993. Four treated artery samples were studied and the results indicated that treated arteries did not show a clot during the 10 minute test interval.

Example 2

Freshly harvested bovine pericardium was stored in 50% alcohol for one week and then treated in a solution containing 5% PEG, 0.5% hydrogen peroxide, 4 M NaCl and 0.05 M phosphate buffered at pH 7.0 for 48 hours at 4° C. The pericardial tissues were washed in 50% ethanol twice and then further treated in a solution of indomethacin (50 mg/l) and heparin (250 IU/ml) in 50% ethanol overnight. The treated pericardial tissues were further soaked in 50% ethanol containing 20% glycerol, 5% PEG (MW=10,000), indomethacin (50 mg/l), and heparin (250 IU/ml). The pericardial tissues were then freeze-dried using a FTS Durastop/Duratop lyophilyzer system. The freeze-dried pericardial tissues were subjected to hydrogen peroxide sterilization by Star Service (Hayward, Calif.) with a Sterrad-100 hydrogen peroxide gas phase sterilizer using a standard validated sterilization program. The tissues were rinsed in saline for 30 minutes before the following study was done:

1. Cell Adhesion and Attachment Study—this study was conducted using a standard cell culture protocol. The study was done by growing smooth muscle cells, fibroblasts or endothelial cells on treated bovine pericardium. Treated pericardial tissues were used in order to provide a flat surface for cell culture studies. Results demonstrate that the treated tissues are non-toxic and support the attachment, adherence and proliferation of these different cell types.

2. In a separate study, treated pericardial and control tissues treated with gluatarldehyde placed on top of culture dishes with confluent cells. Glutaraldehyde treated pericardial tissue were toxic resulting in most cells dying around the tissues. However, cells surrounding the treated pericardial migrated onto the tissue samples.

Example 3

Bovine mesenteric arteries and porcine mammary arteries were stored in 50% alcohol for one week and then treated in a solution containing 5% PEG, 0.5% hydrogen peroxide, 4 M NaCl and 0.05 M phosphate buffered at pH 7.0 for 48 hours at 4° C. The arteries were washed in 50% ethanol twice and then further treated in a solution of indomethacin (20 mg/l) and heparin (250 IU/ml) in 50% ethanol overnight. The tissues were rinsed in saline for 30 minutes before the following studies were done:

1. Sheep descending aorta to circumflex coronary artery bypass implant study—treated porcine mammary arteries, glutaraldehyde treated porcine and bovine conduits as well as PTFE grafts were implanted in 10 sheep as descending aorta to circumflex artery bypass for up to 202 days. The results of this study are summarized in the Table 3 below:

TABLE 3

| Animal | Group | PO Days* | | Patency |
|---|---|---|---|---|
| 1 | Treated Porcine Artery | 202 | S | Patent |
| 2 | Treated Porcine Artery | 194 | S | Patent |
| 3 | Treated Porcine Artery | 162 | S | Patent |
| 4 | Treated Porcine Artery | 202 | S | Patent |
| 5 | Treated Porcine Artery | 189 | S | Patent |
| 6 | Glutaraldehyde Treated Porcine Artery | 7 | D | Obstructed |
| 7 | Glutaraldehyde Treated Bovine Artery | 155 | S | Obstructed |
| 8 | Glutaraldehyde Treated Bovine Artery | 16 | D | Obstructed |
| 9 | PTFE | 16 | D | Obstructed |
| 10 | PTFE | 58 | D | Obstructed |

*Post-Operative days: S - Sacrificed, D - Death

2. Sheep ascending aorta to circumflex coronary artery bypass implant study treated bovine and porcine arteries were implanted in 12 sheep as ascending aorta to circumflex artery bypasses. Two sheep were implanted with autologous azygos veins as controls. The purpose of this series is to compare treated arteries to acceptable controls rather than PTFE or glutaraldehyde treated grafts that are known to fail as coronary bypasses. Thirteen animals survived and were sacrificed between 150-172 days. One sheep with a treated artery died at 10 days from a non-graft related event. The results are shown in Table 4 below:

TABLE 4

| Animal | Group | PO Days* | Pat-[1] ency | No Lesion/ Thrombus | Small/ Lesion/ Thrombus[2] | Moderate/ Lesion Thrombus[3] |
|---|---|---|---|---|---|---|
| 3 | Autologous Vein | 168/S | + | + | | |
| 4 | Autoloqous Vein | 165/S | + | + | | |

TABLE 4-continued

| Animal | Group | PO Days* | Pat-[1] ency | No Lesion/ Thrombus | Small/ Lesion/ Thrombus[2] | Moderate/ Lesion Thrombus[3] |
|---|---|---|---|---|---|---|
| 1 | Treated Porcine Artery | 10/D | | | | |
| 2 | Treated Porcine Artery | 172/S | + | | | + |
| 8 | Treated Porcine Artery | 162/S | + | | | + |
| 9 | Treated Porcine Artery | 158/S | + | | | + |
| 10 | Treated Porcine Artery | 151/S | + | + | | |
| 11 | Treated Porcine Artery | 160/S | + | | | + |
| 12 | Treated Porcine Artery | 155/S | + | + | | |
| 5 | Treated Bovine Artery | 162/S | + | | | + |
| 6 | Treated Bovine Artery | 155/S | + | | + | |
| 7 | Treated Bovine Artery | 154/S | + | | + | |
| 13 | Treated Bovine Artery | 152/S | + | + | | |
| 14 | Treated Bovine Artery | 152/S | + | + | | |

Total number of animals survived = 13
*Post Operative days: S - Sacrificed, D - Early Death
1 Patency was confirmed by Angio
2 Small occlusion with thrombus (<1%)
3 Moderate occlusion with thrombus (<10%)

Example 4

Fresh porcine heart valve leaflets stored in 50% alcohol for two weeks were treated in a solution containing 5% PEG, 0.5% hydrogen peroxide, 4 M NaCl and 0.05 M phosphate buffered at pH 7.0 for 48 hours at 4° C. The heart valve leaflets were washed in 50% ethanol twice and then mounted on stents (Labcor Laboratories, Belo Horizonte, Brazil). The mounted valves were further treated in a solution of indomethacin (20 mg/l) and heparin (250 IU/ml) in 50% ethanol overnight. The tissues were rinsed in saline for 30 minutes before implanted as mitral heart valves replacement in juvenile sheep. These implants were recovered after a five-month implant period and the valves were patent with no signs of tissue over growth or calcification. Valve leaflet tissues were covered with lining cells consistent with endothelial cells.

While I have shown and described examples and embodiments of a method of treatment of collagenous connective tissue for implant into a recipient without an immune or inflammatory rejection, it is to be understood that the method is subject to many modifications without departing from the scope and spirit of the claims as recited herein.

What is claimed:

1. A method for processing collagenous connective tissue having a structure of collagen fibers from an animal donor source such that upon implant of said tissue into a recipient said tissue is acceptable to the recipient without an immune and inflammatory rejection, comprising the steps of:
   (a) stabilizing the collagen fibers contained in said collagenous connective tissue in a cold stabilizing solution for a period of time and at a temperature sufficient to retain the structure of the collagen fibers where said temperature range is 4 to 10 degrees centigrade;
   (b) soaking said collagenous connective tissue in a first solution comprising predetermined quantities and concentrations of polyglycol, an oxidizing agent, salt and phosphate buffer at a predetermined temperature where said first solution is of sufficient ionic strength to permit ground substances to dissociate from said collagenous connective tissue such that the collagen fibers remain stable;
   (c) after step (b), washing said collagenous connective tissue in predetermined quantities and concentrations of a second solution comprising alcohol and water for a sufficient period of time at a predetermined temperature to sufficiently remove the residue of said first solution therefrom;
   (d) soaking said collagenous connective tissue in a third solution comprising a predetermined quantity and concentration of an anti-inflammatory agent at a predetermined temperature; and
   (e) soaking said collagenous connective tissue in a fourth solution comprising a predetermined quantity and concentration of an anti-thrombic agent at a predetermined temperature.

2. The method recited in claim 1 wherein said polyglycol is selected from the group consisting of polyethylene glycol and polypropylene glycol.

3. The method recited in claim 1 wherein said salt is selected from the group consisting of sodium chloride, potassium chloride, sodium bromide, potassium bromide, sodium sulfate, potassium sulfate, ammonium chloride and ammonium sulfate.

4. The method recited in claim 1 wherein said oxidizing agent is hydrogen peroxide.

5. The method recited in claim 1 wherein said anti-inflammatory agent is selected from the group consisting of indomethacin, ibuprofin, aspirin, choline salicylate, difunisal, magnesium salicylate, magnesium choline salicylate, salsalate, flurbiprofen, fenoprofen, ketoprofen, naprosen, naproxen sodium, oxaprozin, diclofenac sodium, diclofenac misoprostol, etodolac, indocin, ketorolac, natumetone, sulindac, tolmetin, sulfinpyrazone, dipyridamole, ticlopidine, valdecoxib, rofecoxib, piroxicam, meloxicam, meclofenamate sodium, mefenamic, cyclophosphamide, cyclosporine microemulsion, chlorambucil, anagrelide, clopidogrel, and cilostazol.

6. The method recited in claim 1 wherein said anti-inflammatory agent in said third solution is an analgesic.

7. The method recited in claim 1 wherein said antiinflammatory agent in said third solution is an antipyretic.

8. The method recited in claim 1 wherein the temperature of said third solution is in the range of 4 to 25 degrees Centigrade.

9. The method recited in claim 1 wherein said anti-thrombic agent in said fourth solution is selected from the group consisting of heparin, ardeparin, enoxaparin, tinzaparin, danapariod, lepiruden and hirudin.

10. The method recited in claim 1 wherein said anti-thrombic agent is an anticoagulant.

11. The method recited in claim 1 wherein said alcohol in said second solution is selected from the group consisting of ethanol, iso-propanol, and n-propanol.

12. The method recited in claim 1 wherein the concentration of said alcohol in said second solution is in the range of 25% to 75%.

13. The method recited in claim 1 wherein the concentration of said salt in said first solution is in the range of 2.5M to 4.5M.

14. The method recited in claim 1 wherein the concentration of said oxidizing agent in said first solution is in the range of 0.1% to 2%.

15. The method recited in claim 1 wherein the temperature of said cold stabilizing solution is in the range of 4 to 10 degrees Centigrade.

16. The method recited in claim 15 wherein said cold stabilizing solution is a saline solution, further comprising soaking said collagenous connective tissue in said saline solution for a period less than 48 hours.

17. The method recited in claim 15 wherein said cold stabilizing solution is an alcohol and water solution, further comprising soaking said collagenous connective tissue in said alcohol and water solution for a period less than 30 days.

18. The method recited in claim 16 further comprising, after the step recited in claim 16, placing said collagenous connective tissue in an alcohol solution and soaking said collagenous connective tissue therein for a period less than 30 days.

19. The method recited in claim 1 wherein said tissue is soaked in said first solution for a period in the range of 12 hours to 14 days.

20. The method of claim 1 where said phosphate buffer is selected from the group consisting of sodium phosphate and potassium phosphate.

21. The method of claim 1 wherein the concentration of said phosphate buffer is in the range of 0.02 to 0.1M with a pH in the range of 6.5 to 7.8.

22. The method recited in claim 1 further comprising the steps of soaking said collagenous connective tissue in a 50% ethanol solution containing predetermined quantities and concentrations of glycerol, polyethylene glycol, indomethacin, and heparin, freeze-drying said collagenous connective tissue with a lyophilyzer system, and sterilizing said collagenous connective tissue with a hydrogen peroxide gas phase sterilizer.

23. The method recited in claim 1 further comprising the steps of freeze-drying said collagenous connective tissue with a lyophilyzer system, and sterilizing said collagenous connective tissue with a hydrogen peroxide gas phase sterilizer.

24. The method recited in claim 1 wherein said oxidizing agent is ozone.

25. The method recited in claim 24 wherein the range of concentration of said oxidizing agent is in the range of 1-500 ppm.

26. The method recited in claim 1 wherein the concentration of said anti-inflammatory agent in said third solution is in the range of 10 to 200 mg/liter.

27. The method recited in claim 1 wherein the concentration of said anti-thrombic agent in said fourth solution is in the range of 100 to 1000 IU/ml.

28. The method recited in claim 1 wherein the concentration of said polyglycol in said first solution is in the range of 1% to 15% and the molecular weight of said polyglycol is in the range of 2,000 Daltons to 20,000 Daltons.

* * * * *